United States Patent
Wong et al.

(10) Patent No.: US 8,803,682 B2
(45) Date of Patent: Aug. 12, 2014

(54) SLEEP-POSTURE SENSING AND MONITORING SYSTEM

(75) Inventors: Tit-Shing Wong, Kowloon (CN); Sui-kay Wong, North Point (CN); Lewie Wai-choi Leung, Sai Kung (CN)

(73) Assignee: J.T. Labs Limited, On Lok Tsuen Fanling (CN)

( * ) Notice: Subject to any disclaimer, the term of this patent is extended or adjusted under 35 U.S.C. 154(b) by 343 days.

(21) Appl. No.: 13/311,666

(22) Filed: Dec. 6, 2011

(65) Prior Publication Data

US 2012/0139722 A1   Jun. 7, 2012

Related U.S. Application Data

(60) Provisional application No. 61/459,093, filed on Dec. 7, 2010.

(51) Int. Cl.
*G08B 1/08* (2006.01)
*A61B 5/11* (2006.01)
*A61B 5/00* (2006.01)

(52) U.S. Cl.
CPC ............. *A61B 5/1116* (2013.01); *A61B 5/4818* (2013.01); *A61B 5/4806* (2013.01); *A61B 5/74* (2013.01); *A61B 5/0002* (2013.01); *A61B 2562/0219* (2013.01); *A61B 5/6817* (2013.01); *A61B 2560/0412* (2013.01); *A61B 5/6803* (2013.01); *A61B 5/6831* (2013.01); *A61B 5/6823* (2013.01); *A61B 5/6824* (2013.01); *A61B 5/7405* (2013.01)
USPC ... 340/539.12; 340/438; 340/439; 340/573.1; 340/686.1; 340/686.2

(58) Field of Classification Search
USPC .............. 340/539.12, 438, 439, 573.1, 686.1, 340/686.2, 575, 576
See application file for complete search history.

(56) References Cited

U.S. PATENT DOCUMENTS

| | | |
|---|---|---|
| 1,282,980 A | 10/1918 | Takach |
| 4,542,547 A | 9/1985 | Sato |
| 4,805,633 A | 2/1989 | Kotani et al. |
| 5,170,364 A | 12/1992 | Gross et al. |
| 5,560,374 A | 10/1996 | Viard |
| 5,577,399 A | 11/1996 | Whipple et al. |
| 5,630,238 A | 5/1997 | Weismiller et al. |
| 5,787,531 A | 8/1998 | Pepe |
| 5,794,289 A | 8/1998 | Wortman et al. |
| 5,963,997 A | 10/1999 | Hagopian |
| 5,966,763 A | 10/1999 | Thomas et al. |

(Continued)

FOREIGN PATENT DOCUMENTS

| | | |
|---|---|---|
| CN | 1409646 | 4/2003 |
| CN | 1741782 | 3/2006 |

(Continued)

*Primary Examiner* — Daryl Pope
(74) *Attorney, Agent, or Firm* — R. Neil Sudol; Henry D. Coleman

(57) ABSTRACT

In a system for protecting a user from injury sustained during sleep, a sensing device is operated to automatically monitor orientation or posture of a user during sleep of the user. A signal is transmitted from the sensing device to a control unit, which is operated to activate an appliance so that the appliance generates an alert signal upon detection by the sensing device and control unit of an undesirable orientation or posture of the user.

15 Claims, 3 Drawing Sheets

(56) References Cited

U.S. PATENT DOCUMENTS

| | | | |
|---|---|---|---|
| 6,047,424 A | 4/2000 | Osborne et al. | |
| 6,108,843 A | 8/2000 | Suzuki et al. | |
| 6,119,291 A | 9/2000 | Osborne et al. | |
| 6,154,907 A | 12/2000 | Cinquin | |
| 6,353,950 B1 | 3/2002 | Bartlett et al. | |
| 6,421,858 B1 | 7/2002 | Cuerel | |
| 6,668,408 B2 | 12/2003 | Ferrand et al. | |
| 6,721,980 B1 | 4/2004 | Price et al. | |
| 7,107,642 B2 | 9/2006 | Wong et al. | |
| 7,204,250 B1 | 4/2007 | Burton | |
| 7,214,185 B1 | 5/2007 | Rosney et al. | |
| 2002/0039008 A1 | 4/2002 | Edgar et al. | |
| 2002/0070866 A1 | 6/2002 | Newham | |
| 2004/0163648 A1 | 8/2004 | Burton | |
| 2004/0177449 A1 | 9/2004 | Wong | |
| 2005/0248462 A1* | 11/2005 | Cece et al. | 340/575 |
| 2006/0162074 A1 | 7/2006 | Bader | |
| 2010/0031072 A1* | 2/2010 | Hung et al. | 713/323 |
| 2010/0147304 A1 | 6/2010 | Burton | |
| 2011/0100366 A1 | 5/2011 | Chou | |

FOREIGN PATENT DOCUMENTS

| | | |
|---|---|---|
| CN | 1777381 | 5/2006 |
| CN | 1961829 | 5/2007 |
| CN | 101204345 | 6/2008 |
| CN | 101393058 | 3/2009 |
| CN | 101548833 | 10/2009 |
| CN | 101618247 | 1/2010 |
| CN | 201403927 | 2/2010 |
| CN | 101697935 A | 4/2010 |
| EP | 0489310 | 6/1992 |
| WO | WO 0024353 | 5/2000 |

* cited by examiner

SLEEP-POSTURE SENSING AND MONITORING SYSTEM

BACKGROUND OF THE INVENTION

This invention relates to a system that automatically monitors a user's sleeping pose or orientation.

Sleeping occupies almost ⅓ of a person's lifetime. Bad sleep posture can cause health problems such as shoulder pain, neck pain, poor blood circulation particularly in elderly people and, in a worst case, suffocation of babies.

There is a need for a simple and cost effective system for improving sleep quality and preventing or at least minimizing unwanted sleep poses.

SUMMARY OF THE INVENTION

The present invention aims to provide a system for improving sleep quality by preventing or at least minimizing unwanted sleep postures or positions. Preferably, the system is simple, cost effective, easy to use and reliable.

The present invention provides for the automatic monitoring of a person during sleep to ascertain when the person adopts or settles into an undesirable body configuration, that is, a body configuration that is likely to eventually result in a chronic pain or one sort or another, if the person remains too long in the undesirable configuration.

The present invention contemplates a sensing system that detects body orientation or posture and provides a stimulus to the sleeping person, via a control unit and an alert signal generator such as a radio, light, or other electrical appliance. The stimulus is effective to cause the sleeping person to change his or her sleep posture to a pose that is not deemed to cause pain of one sort or another.

The sleeping pose sensing system of the present invention is configured to differentiate and identify sleeping poses including, but not limited to, flat on the back, flat on the stomach, and on the left side or the right side, or some orientation in between, for example, where the head is inclined to one side while the back is horizontal on the bed surface.

The sensing system preferably includes a sensor that is placed into contact with the body of a user. The sensor may be an accelerometer, a position ball switch, a bubble switch, a gyroscope, an integrated-circuit gyroscope, but is not limited to these devices. The sensor may be any device that is capable of providing position information. For instance, a user may be provided with sensors in the form of wireless signal transmitters that are attached to predetermined or recordable locations on the user's body. A control unit receiving the signals is able to triangulate the user's orientation or posture from the signals received from the transmitters.

The position sensors are typically mounted to carriers that in turn are attachable to the user at predetermined areas of the user's anatomy. The carriers may take different forms, depending on the respective anatomical home sites. Headbands, earplugs, and eye patches or eyeshades, are adapted for attaching sensors to the user's head. Adhesive patches can be used on the torso, for example, for application to the chest, back or shoulders.

A sensor for use in a sleep pose sensing system in accordance with the present invention may be designed for detecting orientation of the sensor (horizontal, vertical, in between) and emitting a signal (preferably wireless) that encodes and quantifies the orientation (e.g., an angle relative to the normal). Two such sensors, one extending straight across the chest and another extending from front to back on the rib cage under the armpit are sufficient to define the orientation of the user's torso for most users of the present invention. A control unit need only collate signals from the two sensors to determine torso orientation.

Accordingly, the sensors may emit signals that contain different kinds or amounts of information. The more information the signals contain, the less processing or the fewer calculations that are necessary for control unit to perform. The control unit is programmed to be responsive to the user's sleep posture or orientation and to generate an alert signal that induces the user to change his or her posture (or to change the sleep posture of another person such as a baby, for instance, to turn the baby so that it is not on its stomach). The alert signal may be optical, in the case that a lamp is turned on. Alternatively or additionally, the alert signal may be a wake-up alarm from an alarm clock. Preferably, the alert signal is recognizably different from a wake-up alarm so that the user is quickly aware that he or she should turn or shift on the mattress rather than rising from bed.

An electro-acoustic transducer may be placed in or on the user's pillow or in earplugs (i.e., earphones) so as to alert the user without disturbing other sleepers in the bedroom. Alternatively, a vibration generator may produce a personal alert signal, sensible solely by the user. Such a vibration generator may take the form of a piezoelectric crystal disposable on the bed or pillow surface.

A control unit of a sleep-posture sensing system in accordance with the present invention may be designed to generate the alert signal only temporarily and to give the user time to change his or her orientation in response to the alert signal, before another alert signal is issued. Thus the deactivation of the alert signal may be automatic, without requiring any action of the user except a change in orientation or posture on the sleeping surface.

A control unit of a sleep-posture sensing system in accordance with the present invention may allow some minimal programming by the individual user. Accordingly, control unit may be programmed with a predetermined set of potentially undesirable postures, exemplarily including flat on the back (sleep apnea) and on one side, in the case of a sore or injured shoulder. The user may be prompted to select which of the potential sleep postures the user wishes to avoid. Alternatively or additionally, the control unit may be configured to permit the user to enter and store postures that the user finds unacceptable or otherwise problematic. In this input mode, the user might, for instance, press one or more keys on a keypad or touch a touch screen menu to inform the control unit that a calibration procedure is to take place. The user then assumes the unacceptable posture with the applicable sensors active and in position and waits for a signal from the control unit, e.g., via an alert signal appliance, that the posture has been detected and recorded.

Pursuant to another feature of the present invention, the control unit may incorporate a timer or clock and be programmed (at the factory and/or by the user) to allow a given amount of time in each of a plurality of sleep orientations. Thus, the user may be allowed to sleep in one or more undesirable postures but only for a limited time. This feature of the invention recognizes that certain sleep postures or positions may become problematic but only when held for unduly lengthy periods of time. In addition, this feature may result in longer undisturbed sleep intervals, with an enhanced opportunity for the user to have REM sleep.

In accordance with a further feature of the present invention, the control unit may be configured to detect that the user is restless. For example, the control unit may maintain of a record of successive sleep postures, as well as the times of each. If the changes in posture exceed a predetermined number within a given period of time, the control unit may activate a radio, MP3 player or other source of soothing sound. The control unit may continue to monitor the user's posture and automatically deactivate the radio, MP3 player or other sound source upon detecting that the user has settled into an acceptable posture for a predetermined period of time.

Where the alert signal is provided in the form of a vibration, the sleep-posture sensing system may include a sleep mat that is placed on top of the bed and that includes a two-dimensional array of vibrators. The vibrators are selectively activated to induce the user to move out of different positions, depending on the location of the user on the mat.

In brief, a sleep-posture sensing system in accordance with the present invention senses or calculates the orientation or posture of a sleeping user and generates an activation signal, resulting in a pre-programmed response keyed to the sleeping pose and/or the recorded sleeping pose changing pattern.

A sleep-posture sensing system in accordance with the present invention comprises at least one position or orientation sensor configured to produce a signal encoding information pertaining to an orientation or posture of a user during sleep and a control unit operatively connected to the sensor and operatively connectable to an appliance for changing an operative state of the appliance in response to the signal from the sensor.

The control unit is programmed to respond to at least one undesirable sleeping orientation or posture of the user. The control unit may be provided at the factory with a memory store of sleep posture parameters defining a multiplicity of different postures. In an interactive set-up or calibration phase of operation, the user may select postures that are to be avoided or minimized during sleep.

The control unit is adapted to activate the appliance to generate an alert signal upon the control unit's detecting that the user is in an undesirable sleeping orientation or posture or has been in a particular sleeping orientation or posture for a prescribed time limit.

The appliance may include an electro-optical transducer (as in a lamp), an electro-acoustic transducer (as in a radio or other sound source), and/or an electro-mechanical vibrator, which is disposable on the user's bed so that the user may engage the vibrator.

It is contemplated that the sensor is mounted to a carrier which in turn is attachable to the user. The carrier may be a patch with an adhesive layer, an eyeshade, a headband or an earplug. Of course, multiple sensors on different carriers may be in use simultaneously.

In accordance with another feature of the present invention, the control unit is configured to measure the time that the user is disposed in the various sleep postures. The control unit may be programmed to activate the appliance to generate a soothing stimulus upon determination that the number of the user's posture changes within a predetermined period exceeds a pre-established threshold.

Any one sensor may take the form of an accelerometer, a position ball switch, a bubble switch, a gyroscope, or a gyroscope integrated circuit. These sensors are orientation sensors, each of which emits a signal when the sensor is in a particular orientation.

A method for protecting a user from injury sustained during sleep comprises, in accordance with the present invention, operating a sensing device to automatically monitor orientation or posture of a user during sleep of the user, transmitting a signal from the sensing device to a control unit, and operating the control unit to activate an appliance so that the appliance generates an alert signal upon detection by the sensing device and the control unit of an undesirable orientation or posture of the user.

The method typically includes attaching the sensor to the user. Where the sensor is mounted to a carrier such as a patch, an eyeshade, a headband or an earplug, the attaching of the sensor to the user includes adhesively attaching the patch to a skin surface, placing the eyeshade or headband on the head of the user, or inserting the earplug into an ear canal of the user, respectively.

Pursuant to another feature of the present invention, the method further comprises automatically timing changes in sleep posture of the user and generating a soothing stimulus to relax the user upon a determination that the number of the user's posture changes within a predetermined period exceeds a pre-established threshold.

The alert signal or stimulus may take the form of a change in ambient lighting conditions, a change in ambient sound, or a vibration.

DEFINITIONS

Figure 1:
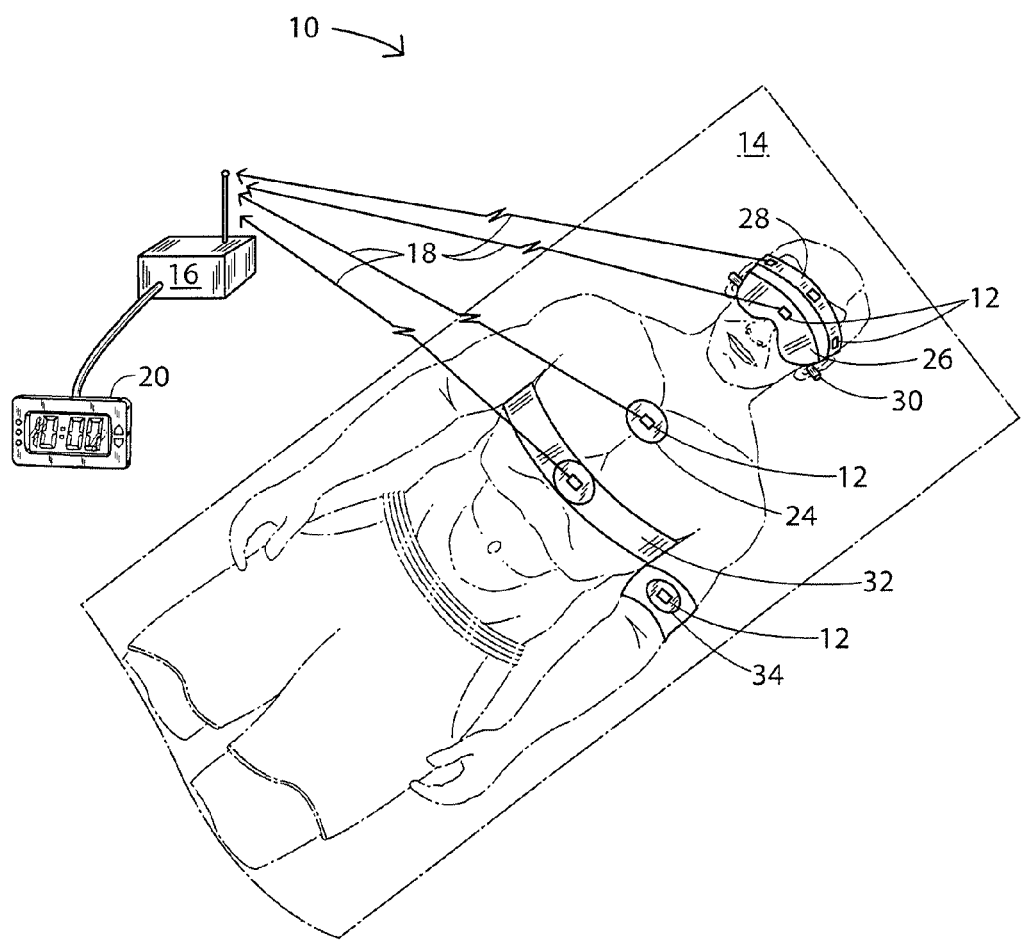
FIG. 1 is a schematic perspective view of a user on a bed, showing the user connected to a sleep-posture monitoring system in accordance with the present invention.

The term "sensor", particularly a position or orientation sensor, is used herein to designate an electrical or electronic element or device that generates an electrical signal encoding information pertinent to a determination of an instantaneous sleep posture a user. The sensor may simply be a wireless signal emitter, where the respective position information is a function of the position of the emitter. Alternatively, the sensor may be an orientation sensor, and include, for instance, one or more gravity switches, a signal transmitter, and a logic circuit coupled to the switch(es) and the transmitter for inducing the emission of a signal when the sensor is moved into a predetermined orientation. Posture or sleep position information may be alternatively or additionally provided by an array of pressure sensors in a mat disposed on the user's bed, as described in U.S. Pat. No. 7,107,642 the disclosure of which is hereby incorporated by reference.

The term "alert signal" is used herein to designate any change in energy that is impinging on a person so as to induce the person to move. An alert signal may be so strong as to awaken the individual. Alternatively, an alert signal may be insufficient to awaken the person but adequate to cause the user to change his or her posture. If the invention is used to monitor the sleeping pose of an infant, in order to prevent sleeping on the stomach, the alert signal is intended to awaken a parent or other caretaker and induce that person to change the sleep posture of the infant.

The term "control unit" is used herein to denote an electronic device that processes electrical signals from position and/or orientation sensors to identify a posture or orientation of a user during sleep or rest and to cause a change in ambient conditions so as to at least subliminally stimulate the user so as to cause the user to change his or her posture. Such a control unit may incorporate or comprise a microprocessor, wherein generic digital processing circuits are modified by programming to execute the monitoring, posture evaluation, and signal activation functions described herein. Alternatively, the control unit may comprise an integrated circuit with component parts hard-wired for signal preprocessing, storing encoded posture data, identifying and encoding sleep postures, timing the duration of sleep postures or positions, evaluating detected postures pursuant to pre-determined acceptability indices, and issuing signals for activating one or more appliances. A combination of hard-wired and generic program-modified circuits is another alternative. Such alternative control unit embodiments are within the ken of those skilled in the art.

The term "appliance" is used herein to denote any electrical, electromechanical, or electrochemical device that is capable of producing energy that, when impinging on a sleeping individual, can cause that individual to change his or her sleeping posture. The production of energy constitutes a change in ambient conditions that may be sensed on a subconscious and optionally conscious level by a sleeping individual. The energy may be electromagnetic radiation, such as a change in ambient light levels. In that case the appliance may be a lamp. Alternatively, the energy may reside in air pressure fluctuations, in which case the appliance may be a radio, a wake-up alarm, an MP3 player, or other sound generator. The sound and light may be generated in combination, as by a television set or computer. Accordingly, an appliance used in the present invention may be an electrical device commonly found in the home and particularly in a bedroom. In another alternative, the appliance is a vibrator that is in effective contact with the user's person. The user might be induced to change position just to avoid the vibration stimulus. Except for a vibrator, an appliance as that term is used herein is typically placed at a remote location from the bed. It is to be noted that an appliance may be used in accordance with the present invention to generate a soothing stimulus or sensation to enhance restfulness, particularly where the user is not truly asleep and is moving around, for instance, as a result of an excess of nervous energy. The soothing stimulus or energy may take the exemplarily form of a sound such as crickets or white noise or a fragrant and calming fragrance. In the latter case, an electrically activatable aerosol dispenser may constitute an appliance operatively connected to the control unit.

The term "carrier" is used herein to denote any element that serves in part to support, contain, hold, or enclose a sensor. A carrier enables or facilitates attachment of the respective sensor or sensors to the person of a user at a predetermined location on the person. A carrier may be a casing, housing, or frame, and include a coupling device. In particular, a carrier for purposes of the present invention may taken the form of an adhesive patch, an eyeshade, an earplug, a headband, an arm band, a chest strap, or an article of clothing (particularly a tightly worn article of clothing, such as a shirt or blouse.

DETAILED DESCRIPTION

As illustrated in FIG. 1, a sleep-posture monitoring or sensing system 10 comprises one or more position or orientation sensors 12 each configured to produce a signal encoding information pertaining to an orientation or posture of a user USR while the user is asleep on a bed 14 or other support. The sleep-posture monitoring or sensing system 10 further comprises a control unit 16 operatively connected to the sensors 12 via wireless signal transmission links 18 and operatively connectable to an appliance 20 for changing an operative state of the appliance in response to the signal from the one or more sensors 12.

Control unit 16 is programmed to respond to at least one undesirable sleeping orientation or posture of the user USR. Control unit 16 may be provided at the factory with a memory store 22 (FIG. 3) of sleep posture parameters defining a multiplicity of different postures. In an interactive set-up or calibration phase of operation, the user USR may select postures that are to be avoided or minimized during sleep.

Control unit 16 is adapted to activate appliance 20 to generate an alert signal upon a detecting by control unit 16 that the user USR is in an undesirable sleeping orientation or posture or has been in a particular sleeping orientation or posture for a prescribed time limit. The activation of appliance 20 by control unit 16 induces the user USR to at least partially awaken and change his or her sleeping posture or pose. The user USR may take the opportunity to deactivate appliance 20. Alternatively, control unit 16 may be designed to de-activate the appliance and terminate the generation of the disturbance.

Sensors 12 are mounted to one or more carriers 23 such as an adhesive patch 24, an eyeshade 26, a headband 28, an earplug 30, a chest band or belt 32, and an arm band 34 each of which in turn is attachable to the user USR. Patch 24 may be a gel pad to minimize discomfort from hard device casings. Of course, multiple sensors 12 on the different carriers may be in use simultaneously.

Sensors 12 may each take the form of an accelerometer, a position ball switch, a bubble switch, a gyroscope, or a gyroscope integrated circuit. Such sensors are orientation sensors, each of which emits a signal when the sensor is in a particular orientation. Alternatively, sensors 12 may simply emit respective wireless electro-magnetic signals that are used by control unit 16 to determine the orientation or posture of the user USR. In that event position information may be determined by triangulation and optionally by signal strength. The signals emitted by sensors 12 differ from one another to identify the parts of the body to which the sensors are appended. For instance, the signals may be pulsed at different frequencies, with different pulse durations, and/or with different inter-pulse intervals.

Figure 2:
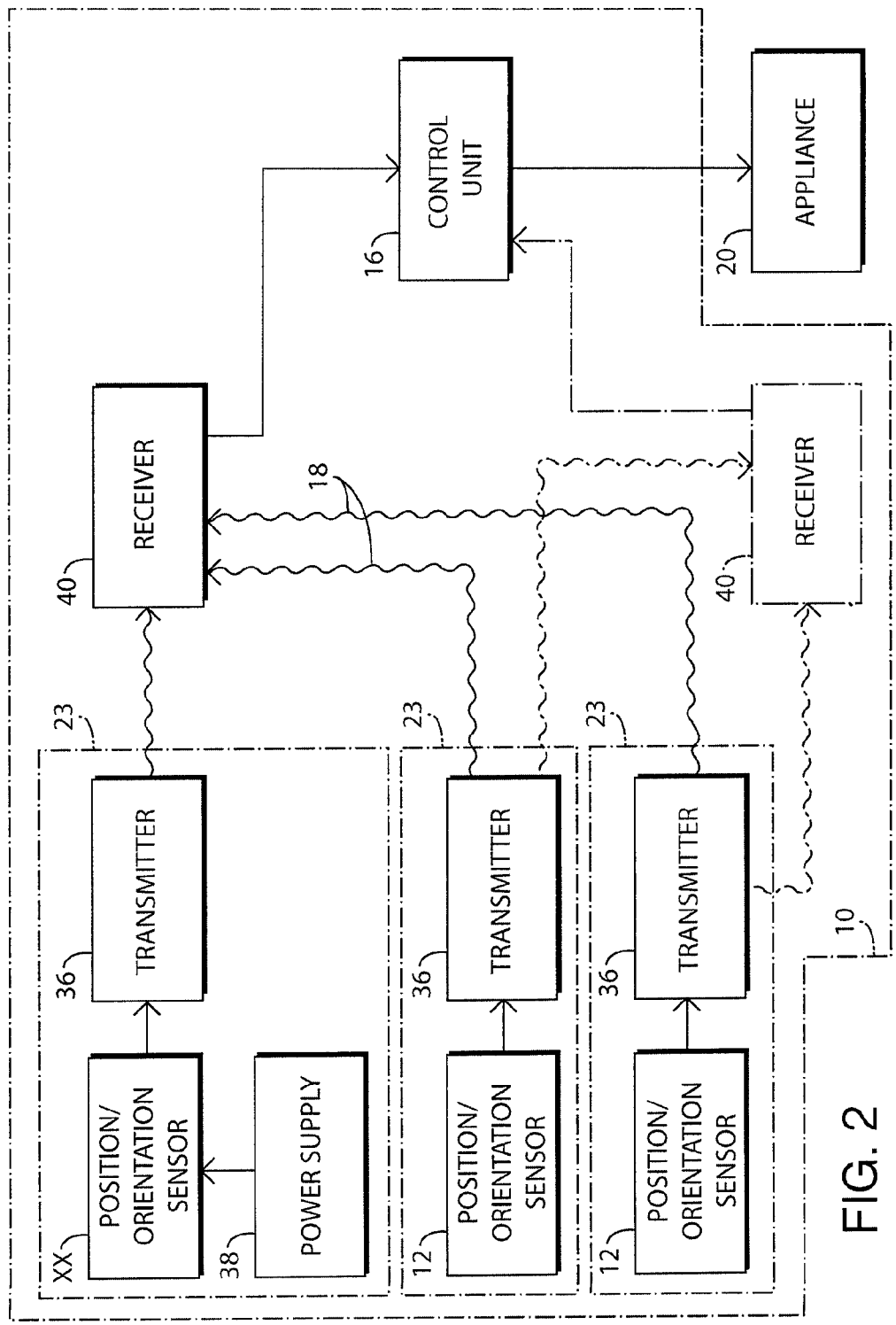
FIG. 2 is a block diagram of functional components of the sleep-posture monitoring system of FIG. 1.

As depicted in FIG. 2, each position or orientation sensor 12 is mounted to a respective carrier 23 together with a wireless transmitter 36 and a power supply 38. Other electronic components may be included as warranted, such as amplifiers, time bases, memories, etc. Wireless signals or links 18 are detected by at least one wireless receiver 40 that is included in or connected to control unit 16. Where triangulation is used to determine sensor location. Two or more receivers 40 are employed.

Figure 3:
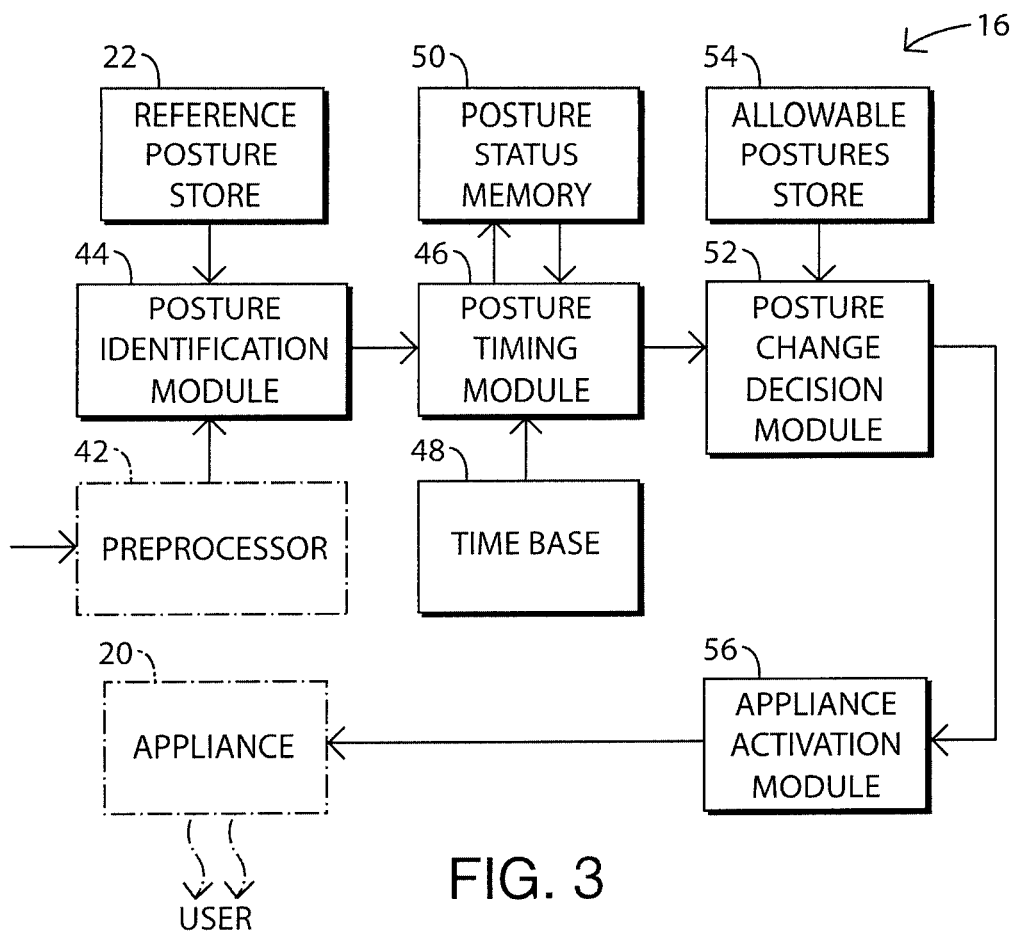
FIG. 3 is a block diagram of selected components of a control unit shown in FIG. 2.

As depicted in FIG. 3, control unit 16 may include a preprocessor 42 that decodes or demodulates and extracts position information from the wireless signals 18 from sensors 12. Where triangulation calculations are required, it is preprocessor 42 that performs those calculations. Preprocessor 42 provides the decoded position and/or orientation information to a posture identification module 44, which consults memory store 22 for indexed reference posture data and, on the basis of that data and the current position or orientation information from preprocessor 42, identifies the sleep posture presently occupied by the user USR. Posture identification module 44 transmits the posture identification or determination to a posture-timing module 46, which in turn is connected to a clock or time base 48 and a posture status memory 50. Posture status memory 50 stores contemporaneous data obtained from posture-timing module 46 and pertaining to the current posture and recent posture history (all during a single night) of the user USR. Posture timing module 46 determines whether the current posture must be changed, pursuant to the rest requirements of the user USR. In some cases, a sleep posture is completely unacceptable so that the smallest time in that posture requires a change in position. In other cases, it may be permissible or desirable for the user USR to occupy that position for a limited time only. Posture-timing module 46 transmits a signal to a posture change decision module 52, which consults a store 54 of data identifying allowable and impermissible postures. Decision module 52 determines whether to activate appliance 20 to awaken or otherwise disturb the user USR so as to cause the user to change position or posture. Decision module 52 transmits a signal to an appliance activation module 56, which typically includes an amplifier section and is connected to appliance 20 to cause that device to change is operative state to provide a stimulus to the user USR.

Figure 4:
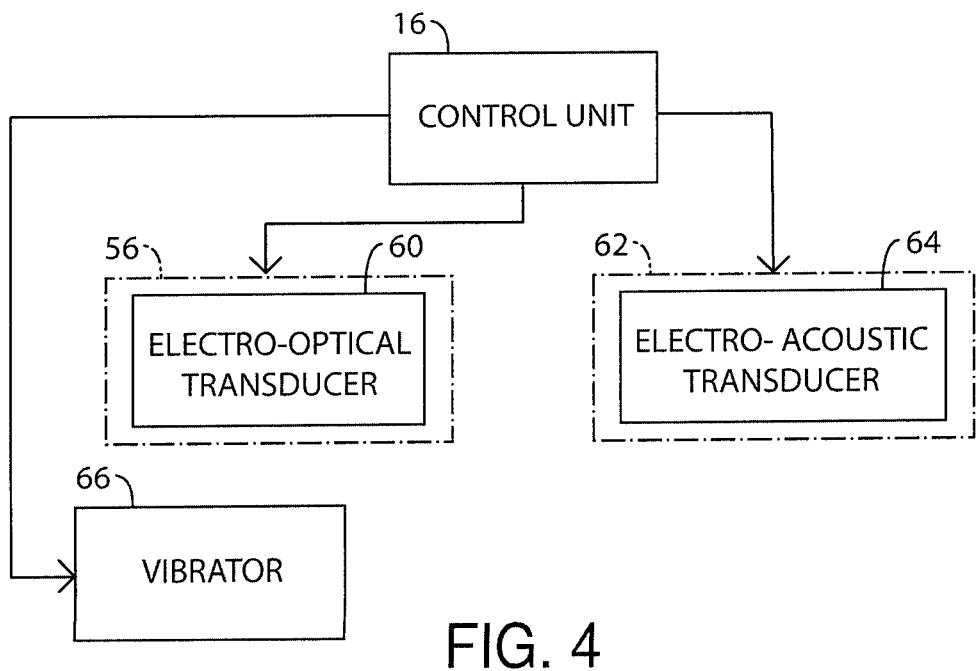
FIG. 4 is a block diagram of a plurality of different alert signal generators serving as the appliance shown in FIGS. 2 and 3.

As depicted in FIG. 4, appliance 20 may be a lamp 58 which includes an electro-optical transducer 60, a radio or other sound source 62 including an electro-acoustic transducer 64, and/or an electro-mechanical vibrator 66, which is disposable on the user's bed 14 so that the user USR may be positioned in contact with the vibrator.

By way of posture-timing module 46, control unit 16 is configured to measure the time that the user USR is disposed in various sleep postures. Control unit 16 and particularly posture change decision module 52 may be configured to activate appliance 20 to generate a soothing stimulus upon determination by posture timing module 46 that the number of the user's posture changes within a predetermined period exceeds a pre-established threshold.

Monitoring or sensing system 10 and particularly posture-timing module 46 may record, in posture status memory 50, the durations of each pose as well the pose change patterns.

Control unit 16 is provided with software that institutes posture analyses via posture identification module 44 and posture-timing module 46 and initiates a response via decision module 52 according to pre-programmed logic. System 10 may be provided with a single or multi ON-OFF power switching control(s) in a predetermined way or pre-programmed response according to the signal received in providing a single or multi ON-OFF power switching control(s) for the user USR to connect to any compatible appliance(s) as wish.

Some examples of operation and use of the monitoring system 10 are:
a. The system switches on an alarm to wake up a parent and switches on a lamp in a baby's bedroom upon a detection that the user USR (the baby) has turned to lie on its stomach.
b. The system activates a radio or an MP3 player to wake up the user USR if he or she should not sleep on his or her left hand side because of poor blood circulation and the system determines that the user has lain in the undesirable position for a time in excess of a pre-established limit.
c. The system energizes the room lights and activates an alarm to wake up the user USR if he or she is sleeping flat on his or her stomach.
d. The system turns on a music player to play some soft music in order to sooth the emotion of the user USR if the user USR keeps changing his/her sleeping pose in a very frequent way, say every few minutes.

The monitoring system of the device may include a single or multiple ON-OFF power switching controls for the user USR to connect to any compatible applianceSs) as desired.

System 10 basically consists of two parts: the pose sensing system (sensors 12 and carriers 23) to be put on or attached to the user USR's body and a monitoring system (control unit 16) which executes a predetermined response(s) in accordance with position and/or orientation signals received from the sensing system.

The sensing system may take various forms and sizes:
a. Sleeping pose sensors 12 may each take the form of an accelerometer, a position ball switch, a bubble switch, a gyroscope, a gyroscope I.C., etc., but are not limited to these devices.
b. Sleeping pose sensors 12 are active system components that may emit intermittent, discrete or continuous signals (such as radio frequency, infrared, ultrasonic sound wave, Bluetooth technology, Wi-Fi technology, etc., but not limited to these types of signals) according to the sleeping pose of the user USR to receivers 40 over a short distance range from 0.1 foot to 50 feet, signal links 18 optionally going through walls or partitions.
c. A sleeping pose sensor 12 may be in the form and size of an "in-ear" ear plug which could completely locate inside the external ear well.
d. A sleeping pose sensor 12 may be encapsulated inside of a normal eyeshade 26 or headband 28.
e. A sleeping pose sensor may be housed entirely inside patch 24 of a size range from 0.5 inch to 4 inches across and with a thickness ranging from 0.1 to 1 inch, and in a one time use or with replaceable self-adhesive backing such as gel, bandage adhesive . . . etc but not limited thereto.

The monitoring system 10 may be powered by a battery, an AC power line, etc. Within the monitoring system, there is electronic firmware with CPU processing capability, the software loaded in the firmware system, which makes analyses and institutes responses according to pre-programmed logic and signal inputs from the sleeping pose sensors 12. The electronic firmware provides outputs in accordance with the software and there may be one or more ON OFF switching channels which are selected and set according to the sleep poses by the user USR to control any compatible appliance(s) such as alarm, radio, light, phone module, etc., but not limited thereto.

Although the invention has been described in terms of particular embodiments and applications, one of ordinary skill in the art, in light of this teaching, can generate additional embodiments and modifications without departing from the spirit of or exceeding the scope of the claimed invention. For example, it is to be appreciated that a sleep posture may be determined by means other than position or orientation sensors attached to the person of the user USR. One such alternative sensing apparatus comprises one or more cameras (arrays of radiation sensors), preferably sensitive to infrared radiation, and a control unit programmed for pattern recognition. Control unit 16 may include a calibration program that is activated by the user USR upon placement of the camera(s) near the user USR's bed and that instructs the user USR to assume a predetermined series of sleep positions in a specific order. The control unit detects, encodes, and stores the successive sleep positions or postures.

Accordingly, it is to be understood that the drawings and descriptions herein are proffered by way of example to facilitate comprehension of the invention and should not be construed to limit the scope thereof.

What is claimed is:
1. A sleep-posture sensing system comprising: at least one position or orientation sensor configured to produce a signal encoding information pertaining to an orientation or posture of a user during sleep; and a control unit operatively con- nected to said at least one position or orientation sensor and operatively connectable to an appliance for changing an operative state of said appliance in response to a signal from said sensor indicating assumption of an undesirable sleeping orientation or posture of the user, said control unit being configured with a time base or clock so as to change the operative state of said appliance only after a predetermined period of time has elapsed after detection of the undesirable sleeping orientation or posture of the user, whereby the user is permitted to sleep for said period of time after the assumption of the undesirable sleeping orientation or posture.

2. The sensing system defined in claim 1 wherein said appliance includes a transducer taken from the group consisting of an electro-optical transducer, an electro-acoustic transducer, and an electro-mechanical vibrator.

3. The sensing system defined in claim 1 wherein said sensor is mounted to a carrier attachable to the user.

4. The sensing system defined in claim 3 wherein said carrier is taken from the group consisting of a patch, an eyeshade, a headband and an earplug.

5. The sensing system defined in claim 1 wherein said appliance is spaced from the user and from a bed on which the user reclines.

6. The sensing system defined in claim 1 wherein said appliance includes a transducer taken from the group consisting of an electro-optical transducer, an electro-acoustic transducer, and an electro-mechanical vibrator.

7. The sensing system defined in claim 1 wherein said sensor is taken from the group consisting of an accelerometer, a position ball switch, a bubble switch, a gyroscope, and a gyroscope integrated circuit.

8. A sleep-posture sensing system comprising: at least one position or orientation sensor configured to produce a signal encoding information pertaining to an orientation or posture of a user during sleep; and a control unit operatively connected to said at least one position or orientation sensor and operatively connectable to an appliance for changing an operative state of said appliance in response to the signal from said sensor, said control unit being configured to time changes in sleep posture and to activate said appliance to generate a soothing stimulus upon determination that the number of the user's posture changes within a predetermined period exceeds a pre-established threshold.

9. A sleep-posture sensing system comprising: at least one position or orientation sensor configured to produce a signal encoding information pertaining to an orientation or posture of a user during sleep; and a control unit operatively connected to said at least one position or orientation sensor and operatively connectable to an appliance for changing an operative state of said appliance in response to the signal from said sensor, said sensor being wirelessly connected to said control unit.

10. A method for protecting a user from injury sustained during sleep, comprising: disposing a sensing device in a bedroom of a user; operating said sensing device to automatically monitor orientation or posture of a user during sleep of said user on a bed in the bedroom; transmitting a signal from said sensing device to a control unit; and operating said control unit to activate an appliance so that said appliance generates an alert signal upon detection by said sensing device and said control unit of an undesirable orientation or posture of the user.

11. The method defined in claim 10 further comprising attaching said sensor to the user.

12. The method defined in claim 11 wherein said sensor is mounted to a carrier taken from the group consisting of a patch, an eyeshade, a headband and an earplug, the attaching of said sensor, the attaching of said sensor to the user including adhesively attaching said patch to a skin surface, placing said eyeshade or headband on the head of the user, or inserting said earplug into an ear canal of the user.

13. The method defined in claim 10, further comprising automatically timing changes in sleep posture of the user and generate a soothing stimulus to relax said user upon determination that the number of the user's posture changes within a predetermined period exceeds a pre-established threshold.

14. The method defined in claim 10 wherein the operating of said control unit to activate said appliance induces said appliance to generate said alert signal taken from the group consisting of change in ambient lighting conditions, a change in ambient sound, and a vibration.

15. The method defined in claim 10 wherein the transmitting of said signal from said sensor to said control unit includes wirelessly transmitting said signal to said control unit.

* * * * *